(12) United States Patent
Castiglioni et al.

(10) Patent No.: US 7,709,681 B2
(45) Date of Patent: May 4, 2010

(54) PROCESS FOR THE PRODUCTION OF TRIMELLITIC ACID

(75) Inventors: Gian Luca Castiglioni, Trescore Balneario (IT); Roberto Pirola, Dalmine (IT); Carlo Fumagalli, Albano Sant'Alessandro (IT)

(73) Assignee: Polynt S.p.A., Scanzorosciate (IT)

( * ) Notice: Subject to any disclaimer, the term of this patent is extended or adjusted under 35 U.S.C. 154(b) by 180 days.

(21) Appl. No.: 11/919,830

(22) PCT Filed: May 6, 2006

(86) PCT No.: PCT/EP2006/004271

§ 371 (c)(1),
(2), (4) Date: Nov. 2, 2007

(87) PCT Pub. No.: WO2006/119939

PCT Pub. Date: Nov. 16, 2006

(65) Prior Publication Data

US 2009/0043124 A1    Feb. 12, 2009

(30) Foreign Application Priority Data

May 13, 2005    (EP) .................................. 05425324

(51) Int. Cl.
*C07C 51/255*    (2006.01)
(52) U.S. Cl. ...................................... 562/413; 562/416
(58) Field of Classification Search ........................ None
See application file for complete search history.

(56) References Cited

U.S. PATENT DOCUMENTS

| | | | |
|---|---|---|---|
| 3,491,144 A | | 1/1970 | Ember et al. |
| 3,532,746 A | * | 10/1970 | Ember ........................ 562/413 |
| 4,755,622 A | | 7/1988 | Schammel et al. |
| 4,992,579 A | | 2/1991 | Schammel et al. |
| 5,250,724 A | * | 10/1993 | Fumagalli et al. ........... 562/416 |

* cited by examiner

*Primary Examiner*—Paul A Zucker
(74) *Attorney, Agent, or Firm*—Polsinelli Shughart PC; Lisa V. Mueller

(57) ABSTRACT

Trimellitic acid is produced by oxidation of pseudocumene in acetic acid at temperatures between 130 and 240° C. in the presence of a catalyst composition containing cobalt, manganese and bromine. The process comprises the stages of:

(i) simultaneously feeding pseudocumene and air or an oxygen-containing gas into a solution containing acetic acid and the catalyst composition, at an addition rate resulting in an oxygen concentration in the off-gas of less than 8 vol %, and at a temperature and a pressure sufficient to result in 5 to 25 mol % of the total amount of oxygen required to oxidize the pseudocumene to trimellitic acid being consumed, and (ii) feeding air or an oxygen-containing gas into the reaction mixture obtained in stage (i) until essentially all of the pseudocumene has been consumed and a molar yield of trimellitic acid of at least 90% has been obtained.

There is no supplementation of catalyst after stage (i).

25 Claims, No Drawings

PROCESS FOR THE PRODUCTION OF TRIMELLITIC ACID

The invention relates to a process for the production of trimellitic acid by catalytic oxidation of pseudocumene. The process is characterized by high yield and improved quality of the crude trimellitic acid obtained.

BACKGROUND OF THE INVENTION

Trimellitic acid (TMA, 1,2,4-benzenetricarboxylic acid) is an important product which finds application as an intermediate in the chemical industry. The most important reaction of tri-mellitic acid is its dehydration to trimellitic anhydride, which in turn is used as a starting material for the production of polymers and chemical intermediates.

Applications of trimellitic anhydride include resins for powder coatings, inks, wire enamels, high performance plasticizers with low volatility, and engineering polymers for high temperature applications.

Trimellitic acid is commercially produced by oxidation of pseudocumene (1,2,4-trimethylbenzene).

All commercial processes oxidize pseudocumene in the liquid phase, in the presence of acetic acid as a solvent and of a catalyst which includes as basic components cobalt, manganese and bromine.

This is the so called Mid Century Catalyst, which was developed in the 1950's and which is applied by most commercial processes for the oxidation of alkyl aromatics (W. Parteheimer, *Catalysis Today*, 1995, 69-158). Terephthalic acid and isophthalic acid are produced according to this technology by liquid phase oxidation of p-xylene and m-xylene, respectively, in the presence of acetic acid as a solvent and of a catalytic system including cobalt, manganese and bromine. In the case of terephthalic acid and isophthalic acid the oxidation reaction is performed in a continuous way. Air and the mixture of solvent, reagent and catalyst are fed continuously to the reactor which operates under pressure and at temperatures in the range of 150 to 200° C. Under these conditions the reagents are oxidized to the corresponding polycarboxylic acids and the reaction mixture is continuously withdrawn from the reactor.

The oxidation of pseudocumene to trimellitic acid is more difficult than the oxidation of p-xylene and m-xylene due to the presence of three methyl groups on the aromatic ring. For this reason a more active catalyst is required in order to obtain acceptable yields and a viable crude quality: in the commercial oxidation of pseudocumene, additional metals, beside manganese and cobalt, are used to increase the activity of the catalyst.

Trimellitic acid, which is the desired product of the reaction, is a poison for the catalyst. For this reason the commercial oxidation of pseudocumene to trimellitic acid is performed batch-wise in order to reach high concentrations of trimellitic acid only in the final stage of the reaction. In the batch process, acetic acid, pseudocumene and catalyst are loaded into the reactor, which is heated up and pressurized. After reaching the desired reaction pressure and temperature, air is fed to the reactor till the oxidation of pseudocumene is completed.

The main drawback of the batch process is that the concentration of the reactant pseudocumene is very high at the beginning of the reaction, when the oxidation is very easy (the oxidation of the first methyl group is easier than the oxidation of the second and the oxidation of this is easier than the oxidation of the third group). In the initial stage the oxidation is difficult to control and the low concentration of dissolved oxygen favors undesired reactions which produce high boiling by-products, and dealkylation and transalkylation reactions which lead to the formation of phthalic acids, in particular isophthalic and terephthalic acid, and pyromellitic acid.

To partially overcome these problems, prior art patents teach the use of a temperature gradient during the batch process: a lower temperature in the first part of the oxidation can prevent the oxygen starvation but cannot avoid the presence of high concentrations of pseudocumene in the first stage of the reaction.

Since the oxidation becomes more difficult going from the first to the second to the third methyl group and since the final oxidation product trimellitic acid is a poison for the catalyst, some patents teach the feed of additional catalyst during the course of the batch oxidation in order to maintain and/or increase the activity of the catalytic system.

U.S. Pat. No. 3,683,016 A describes a batch oxidation of pseudocumene in the presence of a catalyst including cobalt, manganese, cerium and bromine. The first part of the reaction is performed at a lower temperature and part of the catalyst is added stepwise during the batch oxidation of pseudocumene to trimellitic acid.

The use of a temperature gradient and the staged addition of the catalyst is also taught by U.S. Pat. No. 5,250,724 A which uses an improved catalyst including cobalt, manganese, cerium, titanium and bromine.

U.S. Pat. No. 4,755,622 A uses cobalt, manganese, zirconium and bromine as catalyst while the catalyst of U.S. Pat. No. 4,992,579 A contains cobalt, manganese, cerium, zirconium and bromine. These two patents mention, in addition to the temperature gradient and to the staged addition of the catalyst, the possibility of performing the first part of the oxidation in a semi-continuous way: instead of adding all the pseudocumene to the initial reaction mixture, it is gradually fed to the reactor in the first stage of the oxidation. The staged addition of the catalyst foresees the addition of max 35% of total bromine in the first stage, the catalyst added in the second stage includes the total cerium used in the process and part of manganese and zirconium: the compositions of the initial catalyst and of the catalyst added during the reaction are different. The first part of the oxidation, which can be performed in semi-continuous way, is conducted so that the theoretical oxygen uptake is between 1 and 2.5 mol of oxygen/mol hydrocarbon and more preferably between 1.5 and 2 mol of oxygen/mol hydrocarbon. This corresponds to a consumption of oxygen in the semi-continuous stage between 22 and 56% of the theoretical for the preferred condition and between 33 and 44% for the most preferred one.

U.S. Pat. No. 4,992,579 A does not describe the semi-continuous oxidation in the examples.

U.S. Pat. No. 4,755,622 A describes the semi-continuous stage in examples 11 and 13 (both with catalyst staging) and in comparative examples F and H (no catalyst staging). The yield of isophthalic acid plus terephthalic acid (undesired bifunctional byproducts) in most examples is around or over 2 mol %.

In spite of the improvements the quality of the crude trimellitic acid is still not completely satisfactory due to the presence of several byproducts, in particular isophthalic acid and terephthalic acid. A low quality of the crude trimellitic acid is reflected in the final quality of tri-mellitic anhydride and makes the purification of trimellitic anhydride questionable and more difficult. The presence of dibasic acids like terephthalic and isophthalic acid in particular is a main drawback because trimellitic anhydride is used in demanding applications where the presence of bi-functional molecules is detrimental.

The feeding of the catalyst during the batch (second) stage of the oxidation reaction is a complication for the process and leads to an increase of the catalyst consumption. Moreover, when a staged catalyst addition is applied, the composition of the initial catalyst and that of the catalyst added during the reaction are different, this makes impossible the recovery and the recycle of the catalyst contained in the final reaction mixture.

Even with the improvements mentioned in the existing patents, the present processes for the production of trimellitic acid are not completely satisfactory.

SUMMARY OF THE INVENTION

Object of the invention is a novel process for the catalytic oxidation of pseudocumene to tri-mellitic acid, said process being characterized by higher yield and improved quality of crude trimellitic acid.

This object is achieved by carrying out the first part of the reaction in a semi-continuous way, thus avoiding the presence of high concentrations of pseudocumene at the beginning of the oxidation, and by limiting the degree of oxidation of pseudocumene in the semi-continuous stage to no more than 25 percent of the theoretical value corresponding to the complete oxidation to trimellitic acid.

Applicants have found that by this modification of the initial part of the reaction process it is possible to obtain high yields of trimellitic acid and to limit the formation of the most undesired bifunctional byproducts. The modification also avoids the need of feeding catalyst in the second stage of the oxidation reaction.

Ways of Carrying Out the Invention

According to the invention, pseudocumene is fed to a reaction vessel in a first stage while feeding an amount of air or oxygen-containing gas which avoids oxygen starvation and limits the oxygen consumption in this stage to from 5 to 25 percent of the theoretical amount required for the complete conversion of pseudocumene to trimellitic acid. During that stage, the oxygen concentration in the off-gas is held at less than 8 vol %.

In a second stage, air or an oxygen-containing gas is fed into the reaction mixture obtained in the first stage, without supplementation of catalyst, until essentially all of the pseudocumene has been consumed and a molar yield of tri-mellitic acid of at least 90% has been obtained. "Essentially all" means at least 95%, preferably at least 99%.

Operating in this way, at the end of the semi-continuous stage of the oxidation the amount of trimellitic acid is negligible and there are a lot of intermediate products of the oxidation of the methyl groups like alcohols and aldehydes. This avoids catalyst deactivation, and the presence of aldehydes, which are known to co-catalyze the oxidation, favors the completion of the oxidation, thus avoiding the need of an addition of catalyst in the second (batch) stage of the oxidation. According to the invention, all the catalyst is added before the beginning of the oxidation reaction. This is an important simplification of the process, because when there is a staged addition of the catalyst, the catalyst compositions added at the beginning and in the second stage of the reaction are different. This is not only a complication, but makes the recovery and recycle of the catalyst impossible, because the composition of the final catalyst is different from both the composition used at the beginning and that used in the second stage.

The oxidation of pseudocumene to trimellitic acid is performed with air in acetic acid as a solvent and in the presence of a catalyst composition containing at least cobalt, manganese and bromine.

The reaction is carried out at temperatures between 130° C. and 240° C., preferably between 140° C. and 230° C. and at appropriate pressures between 5 and 30 bar, preferably between 6 and 25 bar.

As mentioned above, the first part of the oxidation reaction is carried out as a semi-continuous process, that is, pseudocumene is not loaded into the reactor before starting the oxidation, but is fed gradually and simultaneously with air or an oxygen-containing gas in the first stage of the oxidation reaction.

Preferably the procedure is carried out as follows: Acetic acid and the catalyst are introduced in the reaction vessel. The reaction vessel is closed and the air in it is displaced with nitrogen. Under stirring the pressure is regulated to the desired value with nitrogen and the temperature is increased to the initial reaction temperature, usually between 130° C. and 180° C., preferably between 140° C. and 160° C.

When the desired reaction conditions are reached, the feeding of pseudocumene and air is started. As a rule, the feed of the desired total amount of pseudocumene is completed within 5 to 35 percent of the total reaction time, preferably between 15 and 25 percent of the total reaction time.

During this period the air flow rate is regulated so that the oxygen concentration in the off gases does not exceed 8 vol % and is preferably between 2 vol % and 6 vol %, in order to avoid the formation of explosive mixtures and to reach the desired amount of oxygen consumption in the semi-continuous stage. At the end of the semi-continuous stage, when all the pseudocumene has been fed, the amount of oxygen consumed by the oxidation reaction is between 5 and 25, preferably between 10 and 25 percent of the total amount required for the oxidation of pseudocumene to trimellitic acid.

At the end of the semi-continuous phase the pseudocumene feed is stopped and the air feed is continued to complete the oxidation reaction. During this batch stage the temperature of reaction is conveniently increased to a value between 200° C. and 240° C., preferably between 215° C. and 230° C. In the batch stage there is no feeding of additional catalyst, which makes the handling of the catalyst easier and renders the recovery and recycling of the catalyst possible.

In a preferred embodiment the catalyst composition contains cerium and/or titanium, in addition to cobalt, manganese and bromine.

Preferably the cerium content of the catalyst composition is between 1 and 30 wt %, most preferably between 5 and 20 wt %, relative to the total metal content.

Preferably the titanium content of the catalyst composition is between 0.5 and 13 wt %, most preferably between 3 and 10 wt %, relative to the total metal content.

Preferably the cobalt content of the catalyst composition is between 30 and 70 wt %, most preferably between 40 and 60 wt %, relative to the total metal content.

Preferably the manganese content of the catalyst composition is between 10 and 50 wt %, most preferably between 20 and 40 wt %, relative to the total metal content.

Preferably the total metal concentration comprising cobalt, manganese, and optionally cerium and/or titanium, is between 0.1 and 1 wt %, most preferably between 0.20 and 0.55 wt %, relative to the total amount of pseudocumene employed.

Preferably 0.05 to 0.7 wt %, most preferably between 0.1 and 0.3 wt %, of bromine is employed relative to the total amount of pseudocumene employed.

Advantageously, the metal catalysts are employed in the form of suitable organometallic compounds or alkoxides or in the form of organic or inorganic salts which are easily available and soluble in acetic acid. For example they can be used in the form of acetates, octoates, nitrates, sulfates, chlorides or other salts. Cobalt and manganese are conveniently employed in the form of their acetates, cerium in the form of its nitrate, titanium in the form of its chloride or of an organometallic compound or an alkoxide like tetraisopropyl titanate, tetrabutyl titanate or mixtures thereof. Bromine is usually not employed in elementary form, but in the form of a suitable organic or inorganic compound. Bromides such as ammonium bromide or hydrogen bromide are advantageously employed.

Advantageously the raw material is industrial grade pseudocumene.

The oxidizing agent is advantageously air; one can also use other oxidizing agents with different oxygen content, in particular enriched air with an oxygen content higher than 21 vol %. To avoid formation of explosive mixtures, the oxygen content of the off-gases is preferably kept below 8 vol % during both process stages.

The solvent acetic acid may contain up to 10 wt % (preferably between 2.5 and 7.5 wt %) of water and is customarily employed in a weight ratio of acetic acid to total added pseudocumene of 1:1 to 4:1 (preferably 1.5:1 to 3:1).

The invention is further illustrated by the following non-limiting examples. All experiments were performed in a 5 L titanium autoclave equipped with efficient stirring, overhead condenser, reflux line for the condensate, feeding lines for air and pseudocumene, temperature and pressure control, and on-line analyzers for oxygen, CO and $CO_2$ in the off gases.

EXAMPLE 1

In the autoclave were introduced 1212 g of acetic acid (water content 5.6 wt %), 4.19 g of cobalt acetate tetrahydrate, 2.82 g of manganese acetate tetrahydrate, 1.09 g of ammonium bromide, 0.77 g of cerium nitrate hexahydrate and 0.87 g of a mixture of tetraisopropyl titanate and tetrabutyl titanate (Ti content 16 wt %).

The autoclave was closed and nitrogen was fed to remove air. Temperature and pressure were increased to 8 bar and 160° C. under stirring before starting pseudocumene and air feed.

540 g of pseudocumene were fed in 14 minutes by a piston metering pump; air flow was regulated through a mass flow meter at 2380 NL/h.

After 14 minutes the pseudocumene feed was stopped while the air feed was continued at the same rate.

At this point the oxygen consumed by the reaction corresponded to 20% of the amount required for the complete oxidation of pseudocumene to trimellitic acid.

After stopping the pseudocumene feed, the pressure was gradually increased up to 25 bar in order to raise the temperature up to 225° C.

After about 60 minutes from the start the air flow was gradually reduced in order to keep the $O_2$ content in the off-gases below 5.0 vol %. The total duration of the run was 75 minutes.

After cooling down to room temperature and depressurizing to ambient pressure, the product of the reaction was analyzed by gas chromatography (GC) and high pressure liquid chromatography (HPLC) for the organic components.

The conversion of pseudocumene was complete. The molar yields of desired product and by-products are given in Table 1.

After filtration the crude TMA filter cake was dried and analyzed by HPLC. The weight composition of the dried solid is given in Table 1. It can be noted that, beside the good yield, the formation of the undesired bi-functional byproducts isophthalic and terephthalic acid is low and the purity of crude trimellitic acid is high (around 98 wt %).

EXAMPLE 2

The procedure of Example 1 was repeated but the temperature of the semi-continuous stage was 150° C. and the pressure 7 bar.

At the end of the semi-continuous stage the oxygen consumed by the reaction corresponded to 19% of the amount required for the complete oxidation of pseudocumene to trimellitic acid.

The yields and the product composition are given in Table 1.

TABLE 1

|  | Ex. 1 | Ex. 2 |
|---|---|---|
| TMA yield [mol %] | 92.3 | 92.6 |
| IPA + TPA yield [mol %] | 1.2 | 1.2 |
| mFT yield [mol %] | 0.1 | <0.1 |
| Others yield [mol %] | 2.4 | 2.6 |
| $CO_x$ [wt %] | 4.0 | 3.6 |
| Dried solid: |  |  |
| TMA [wt %] | 97.9 | 98.1 |
| IPA + TPA [wt %] | 0.6 | 0.6 |
| mFT [ppm] | <300 | <100 |
| others [wt %] | 1.4 | 1.3 |

TMA = Trimellitic Acid; IPA = Isophthalic Acid; TPA = Terephthalic Acid; mFT = Methyl-phthalic Acids.

COMPARATIVE EXAMPLE 1

Semi-continuous, Staged Addition of the Catalyst

The reaction was carried out as described in Example 1 but the catalyst addition was staged. Before starting the feed of pseudocumene in the reactor were introduced 1212 g of acetic acid (water content 5.6 wt %), 2.81 g of cobalt acetate tetrahydrate, 1.89 g of manganese acetate tetrahydrate, 0.732 g of ammonium bromide, 0.515 g of cerium nitrate hexahydrate and 0.583 g of a mixture of tetraisopropyl titanate and tetrabutyl titanate (Ti content 16%).

The autoclave was closed and the air was displaced with nitrogen. Temperature and pressure were increased to 8 bar and 160° C. under stirring, before starting pseudocumene and air feed. 540 g of pseudocumene were fed in 14 minutes by a piston metering pump; the air flow was regulated through a mass flow meter at 2380 NL/h.

At this point the oxygen consumed by the reaction corresponded to 20% of the amount required for the oxidation of pseudocumene to trimellitic acid.

After completion of the pseudocumene feed the air feed was continued at the same rate and the pressure was gradually increased up to 25 bar in order to raise the temperature up to 224° C. and then an aqueous solution of cobalt acetate tetrahydrate, manganese acetate tetrahydrate, ammonium bromide and cerium nitrate hexahydrate was fed to the reactor till the end of the reaction. The total amount of salts added was: 1.53 g of cobalt acetate tetrahydrate, 1.03 g of manganese acetate tetrahydrate, 0.397 g of ammonium bromide, 0.279 g of cerium nitrate hexahydrate and 16 g of water.

After about 60 minutes from the start the air flow was gradually reduced in order to keep the $O_2$ content in the off-gases below 5.0 vol %. Total duration of the run was 72 minutes.

After cooling down to room temperature and depressurizing to ambient pressure, the product of the reaction was analyzed by GC and HPLC for the organic components.

The conversion of pseudocumene was complete. The yields and the product composition are given in Table 2.

COMPARATIVE EXAMPLE 2

Semi-continuous, High Conversion at the End of the Semi-continuous Stage

The procedure of Example 1 was repeated but the temperature of the semi-continuous stage was 170° C., the pressure 9 bar and pseudocumene was fed in 20 minutes. At the end of the feed of pseudocumene, the oxygen consumed by the reaction corresponded to 30% of the amount required for the oxidation of pseudocumene to trimellitic acid.

The yields and the product composition are given in Table 2.

COMPARATIVE EXAMPLE 3

Batch, Staged Addition of the Catalyst

The procedure of Example 1 was repeated, but all the pseudocumene was loaded at the beginning, together with the solvent. The catalyst was added partly at the beginning and partly in the second part of the reaction. At the beginning were loaded into the reactor 4.18 g of cobalt acetate tetrahydrate, 2.64 g of manganese acetate tetrahydrate, 0.54 g of ammonium bromide, 0.118 g of cerium nitrate hexahydrate and 0.866 g of a mixture of tetraisopropyl titanate and tetrabutyl titanate (Ti content 16%).

After 1 minute, an aqueous solution of manganese acetate tetrahydrate, ammonium bromide, and cerium acetate hexahydrate was fed to the reactor till the end of the reaction. Total duration of the run was 75 minutes. The total amount of salts added was: 0.166 g of manganese acetate tetrahydrate, 0.529 g of ammonium bromide, 0.627 g of cerium nitrate hexahydrate and 12 g of water.

After cooling down to room temperature and depressurizing to ambient pressure, the product of the reaction was analyzed by GC and HPLC for the organic components.

The yields and the product composition are given in Table 2.

TABLE 2

|  | Comp. Ex. 1 | Comp. Ex. 2 | Comp. Ex. 3 |
| --- | --- | --- | --- |
| TMA yield [mol %] | 89.6 | 91.0 | 88.3 |
| IPA + TPA yield [mol %] | 1.7 | 1.4 | 1.4 |
| mFT yield [mol %] | <0.1 | <0.1 | <0.1 |
| Others yield [mol %] | 3.5 | 3.5 | 3.2 |
| $CO_x$ [wt %] | 5.2 | 4.0 | 7.0 |
| Dried solid: | | | |
| TMA [wt %] | 96.8 | 96.8 | 97.3 |
| IPA + TPA [wt %] | 0.9 | 0.8 | 0.8 |
| mFT [ppm] | <250 | <250 | <100 |
| others [wt %] | 2.3 | 2.5 | 2.0 |

TMA = Trimellitic Acid; IPA = Isophthalic Acid; TPA = Terephthalic Acid; mFT = Methyl-phthalic Acids.

The invention claimed is:

1. A process for the production of trimellitic acid by oxidation of pseudocumene in acetic acid at temperatures between 130 and 240° C. in the presence of a catalyst composition containing cobalt, manganese and bromine, said process comprising the stages of
    (i) gradually and simultaneously feeding pseudocumene and air or an oxygen-containing gas into a solution containing acetic acid and said catalyst composition, at an addition rate resulting in an oxygen concentration in the off-gas of less than 8 vol %, and at a temperature and a pressure sufficient to result in 5 to 25 mol % of the total amount of oxygen required to oxidize the pseudocumene to trimellitic acid being consumed, and
    (ii) feeding air or an oxygen-containing gas into the reaction mixture obtained in stage (i) until essentially all of the pseudocumene has been consumed and a molar yield of trimellitic acid of at least 90% has been obtained, wherein there is no supplementation of catalyst after the completion of stage (i).

2. The process of claim 1, wherein the reaction temperature in stage (i) is between 130° C. and 180° C.

3. The process of claim 1, wherein in the course of stage (ii) the reaction temperature is increased to a final value between 200° C. and 240° C.

4. The process of claim 1, wherein the pressure is between 5 and 30 bar.

5. The process of claim 1, wherein the oxygen concentration of the off gases during stage (i) is from 2 to 6 vol %.

6. The process of claim 1, wherein the catalyst composition further contains cerium and/or titanium.

7. The process of claim 6, wherein the cerium content of the catalyst composition is 1 to 30 wt % relative to the total metal content.

8. The process of claim 6, wherein the titanium content of the catalyst composition is 0.5 to 13 wt % relative to the total metal content.

9. The process of claim 1, wherein the cobalt content of the catalyst composition is 30 to 70 wt % relative to the total metal content.

10. The process of claim 1, wherein the manganese content of the catalyst composition is 10 to 50 wt % relative to the total metal content.

11. The process of claim 1, wherein the total metal concentration comprising cobalt, and manganese, is 0.1 to 1.0 wt % relative to the total amount of pseudocumene employed.

12. The process of claim 6, wherein the total metal concentration comprising cobalt, manganese and cerium and/or titanium is 0.1 to 1.0 wt % relative to the total amount of pseudocumene employed.

13. The process of claim 1, wherein the bromine concentration is 0.05 to 0.7 wt % relative to the total amount of pseudocumene employed.

14. The process of claim 1, wherein the weight ratio of acetic acid to total added pseudocumene is 1:1 to 4:1.

15. The process of claim 2, wherein the reaction temperature in stage (i) is between 140° C. and 160° C.

16. The process of claim 3, wherein in the course of stage (ii) the reaction temperature is increased to a final value between 215° C. and 230° C.

17. The process of claim 4, wherein the pressure is between 6 and 25 bar.

18. The process of claim 7, wherein the cerium content of the catalyst composition is 5 to 20 wt % relative to the total metal content.

19. The process of claim 8, wherein the titanium content of the catalyst composition is 3 to 10 wt % relative to the total metal content.

20. The process of claim 9, wherein the cobalt content of the catalyst composition is 40 to 60 wt % relative to the total metal content.

21. The process of claim 10, wherein the manganese content of the catalyst composition is 20 to 40 wt % relative to the total metal content.

22. The process of claim 11, wherein the total metal concentration comprising cobalt, and manganese, is 0.20 to 0.55 wt % relative to the total amount of pseudocumene employed.

23. The process of claim 12, wherein the total metal concentration comprising cobalt, manganese and cerium and/or titanium is 0.20 to 0.55 wt % relative to the total amount of pseudocumene employed.

24. The process of claim 13, wherein the bromine concentration is 0.1 to 0.3 wt % relative to the total amount of pseudocumene employed.

25. The process of claim 14, wherein the weight ratio of acetic acid to total added pseudocumene is 1:5 to 3:1.

\* \* \* \* \*